(12) United States Patent
Gehlert

(10) Patent No.: US 8,267,972 B1
(45) Date of Patent: Sep. 18, 2012

(54) BONE PLATE

(76) Inventor: Rick J. Gehlert, Albuquerque, NM (US)

( * ) Notice: Subject to any disclaimer, the term of this patent is extended or adjusted under 35 U.S.C. 154(b) by 591 days.

(21) Appl. No.: 11/949,686

(22) Filed: Dec. 3, 2007

Related U.S. Application Data

(60) Provisional application No. 60/868,234, filed on Dec. 1, 2006.

(51) Int. Cl.
A61B 17/58 (2006.01)
A61B 17/56 (2006.01)

(52) U.S. Cl. ..................................................... 606/280

(58) Field of Classification Search .................. 606/69, 606/70, 71, 73, 60, 246–279, 280–299, 300–331
See application file for complete search history.

(56) References Cited

U.S. PATENT DOCUMENTS

| | | | |
|---|---|---|---|
| 2,526,959 A | 10/1950 | Lorenzo | |
| 3,561,437 A | 2/1971 | Orlich | |
| 5,190,544 A * | 3/1993 | Chapman et al. | 606/71 |
| 5,364,398 A | 11/1994 | Chapman et al. | |
| 5,772,662 A | 6/1998 | Chapman et al. | |
| 5,968,047 A | 10/1999 | Reed | |
| 6,695,844 B2 | 2/2004 | Bramlet et al. | |
| D532,515 S | 11/2006 | Buettler et al. | |
| 7,137,987 B2 | 11/2006 | Patterson et al. | |
| 7,267,678 B2 * | 9/2007 | Medoff | 606/62 |
| 7,341,589 B2 * | 3/2008 | Weaver et al. | 606/291 |
| 2002/0156474 A1 * | 10/2002 | Wack et al. | 606/69 |
| 2004/0030339 A1 | 2/2004 | Wack et al. | |
| 2004/0059335 A1 * | 3/2004 | Weaver et al. | 606/69 |
| 2005/0010226 A1 * | 1/2005 | Grady et al. | 606/69 |
| 2006/0116679 A1 | 6/2006 | Lutz et al. | |
| 2006/0173458 A1 * | 8/2006 | Forstein et al. | 606/69 |
| 2006/0217722 A1 * | 9/2006 | Dutoit et al. | 606/69 |
| 2006/0264947 A1 * | 11/2006 | Orbay et al. | 606/69 |
| 2007/0162016 A1 * | 7/2007 | Matityahu | 606/69 |
| 2007/0233106 A1 * | 10/2007 | Horan et al. | 606/69 |
| 2007/0270853 A1 * | 11/2007 | Leung | 606/69 |
| 2008/0300637 A1 * | 12/2008 | Austin et al. | 606/290 |

OTHER PUBLICATIONS

Glassner, Philip J. et al., "Failure of Proximal Femoral Locking Compression Plate: A Case Series", *J. Orthop. Trauma* vol. 25, No. 2 2011, 76-83.

* cited by examiner

Primary Examiner — Kevin T Truong
Assistant Examiner — Christopher Beccia
(74) Attorney, Agent, or Firm — Janeen Vilven; Peacock Myers, P.C.

(57) ABSTRACT

A bone plate assembly and method of use comprising a head; a shaft; an upper surface; a lower surface having a fixed plane intended to be adjacent to the patient's bone when the plate is in use; a first hole positioned in the head wherein the first hole passes through the upper and lower surfaces and is configured to fix a shaft of a first bone anchor along a first axis; a second hole positioned on the anterior portion of the upper surface of the head wherein the second hole passes through the upper and lower surfaces and is configured to fix a shaft of a second bone anchor along a second axis; and a third hole positioned in the posterior side of the head wherein the third hole passes through the upper and lower surfaces and is configured to fix a shaft of a third bone anchor along a third axis, wherein the first axis, the second axis and the third axis do not intersect in the bone when the plate is in use.

20 Claims, 4 Drawing Sheets

BONE PLATE

CROSS-REFERENCE TO RELATED APPLICATIONS

This application claims priority to and the benefit of the filing of U.S. Provisional Patent Application Ser. No. 60/868,234, entitled "Locking Plate", filed on Dec. 1, 2006, and the specification and claims thereof are incorporated herein by reference.

INTRODUCTION

The present invention relates generally to the field of a system and method for treating fractures and nonunions of the proximal femur. More particularly, the present invention relates to a bone plating system utilizing bone anchor technology that is indicated for management of certain fractures and nonunions of the proximal femur.

BACKGROUND OF THE INVENTION

Treatment of fractures and nonunions of the proximal femur collectively have an incidence approaching 300,000 per year in the United States and an associated annual health care burden approaching ten billion dollars. Current implants for these injuries fatigue causing discomfort, risk of further injury and need for reconstruction.

US patent application publication 2005/0010226 describes a locking plate that fastens to the bone using bone anchors. The bone anchors extend into the femoral head, contacting each other at their tips in a truss formation with all of the bone anchor holes lying in the same longitudinal axis on the plate. There are no provisions for managing fracture extension into the femoral neck or isolated vertical femoral neck fracture. An additional concern with this implant is that the proximal body is slender with only a single screw slot in the greater trochanter. This may prevent adequate capture of the greater trochanter in the presence of coronal splitting, a common occurence as documented by Russell in "Skeletal Trauma". Russell T A, Taylor J L. Subtrochanteric fractures of the femur. In: Browner, B D, Levine A M, Jupiter J B, Trafton P F, Eds. *Skeletal Trauma*. Philadelphia: WB Saunders, 1992: 1883-1925.

With intertrochanteric and subtrochanteric extension of a femoral neck fracture cancellous lag screw fixation is not possible. This is because fixed angle constructs are a requirement and sliding compression is undesirable here. Vertical femoral neck fractures are also poorly managed with multiple cancellous lag screws due to the extremely high shear forces across these fractures. A fixed angle construct is more appropriate here as well.

In addition current, proximal femur locking plates do not allow for an ideal screw geometry in the femoral head. As a result, some plates in use have been shown to cause the bone anchors to be exposed as they pass through the greater trochanter and into the femoral head but not through the neck. Further, the most proximal portion of the plate may protrude well above the greater trochanter portion of the femur when applied to femoral neck fractures which may create discomfort to the subject treated with the plate. Aminian et al, Vertically Oriented Femoral Neck Fractures: Mechanical Analysis of Four Fixation Techniques, *Orthopedic Trauma.* 2007, 21: 544-547.

Thus what is needed is an improved system and device to provide an improved treatment for nonunions and fractures of the proximal femur.

Additional objects and advantages of the present invention will be apparent in the following detailed description read in conjunction with the accompanying drawing figures.

SUMMARY OF THE INVENTION

It is an aspect of one embodiment of the present invention to provide a bone plate for treating one or more of the following: subtrochanteric femur fractures, particularly reverse oblique pattern fractures, and those with intertrochanteric or greater trochanter extension and subtrochanteric nonunions as well as isolated vertical femoral neck fractures.

Another aspect of the present invention provides for percutaneous plate insertion to decrease soft tissue dissection, blood loss, and operative time in certain fracture patterns. One embodiment of the present invention provides for an elongated bone plate comprising a head, a shaft, an upper surface, and a lower surface having a fixed plane intended to be adjacent to the patient's bone when the plate is in use. The head comprises a first hole positioned in the head wherein the first hole passes through the upper and lower surfaces and is configured to fix a shaft of a first bone anchor along a first axis; a second hole positioned on the anterior portion of the upper surface of the head wherein the second hole passes through the upper and lower surfaces and is configured to fix a shaft of a second bone anchor along a second axis; and a third hole positioned in the posterior side of the head wherein the third hole passes through the upper and lower surfaces and is configured to fix a shaft of a third bone anchor along a third axis, wherein the first axis, the second axis and the third axis do not intersect in the bone when the plate is in use. In a preferred embodiment the first axis has an angle with the fixed plane that is about 100 degrees (+/−20 degrees) and is directed 10 degrees anterior (+/−20 degrees). In a preferred embodiment the second axis has an angle with the fixed plane that is about 100 degrees (+/−20 degrees) and is directed 5 degrees anterior (+/−20 degrees). In another preferred embodiment the third axis has an angle with the fixed plane that is about 110 degrees (+/−20 degrees) and is directed 5 degrees anterior (+/−20 degrees). For example, the first axis, the second axis and the third axis is fixed by the plate. In addition, the first hole, the second hole, and the third hole may be engineered and designed to have an orientation such that the first axis, the second axis, and the third axis are not surgeon selectable but instead are determined during design of the bone plate.

In an alternative embodiment the bone plate may include a fourth hole positioned in the anterior side of the head wherein the fourth hole passes through the upper and lower surfaces and is configured to fix a shaft of a fourth bone anchor along a fourth axis. Alternatively, the fourth hole may be positioned in the posterior side of the head wherein the fourth hole passes through the upper and lower surfaces and is configured to fix a shaft of a fourth bone anchor along a fourth axis. In yet another alternative embodiment, the fourth hole may be positioned in the proximal shaft wherein the fourth hole passes through the upper and lower surfaces and is configured to fix a shaft of a fourth bone anchor along a fourth axis and has an angle with the fixed plane that is about 45 degrees (+/−20 degrees).

In a preferred embodiment, the head is wider than the shaft. In a more preferred embodiment, at least a portion of the head is curved. In another preferred embodiment the head is between about 2 to about 4 centimeters from anterior to posterior. In another preferred embodiment the head has a thickness of between about 1 to about 5 millimeters.

In another embodiment, the shaft has a thickness of between about 3 to about 15 millimeters. In another embodiment a portion of the shaft has a thickness of between about 6 to 15 millimeters.

Another embodiment of the present invention provides for an elongated bone plate for treating fractures of the proximal femur comprising a head wherein at least a portion of the head is curved; a shaft wherein at least a portion of the shaft is thickened; an upper surface; a lower surface wherein the lower surface has a substantially fixed plane intended to be adjacent to the patient's bone when the plate is in use; a first hole positioned in the head wherein the first hole passes through the upper and lower surfaces and is configured to fix a shaft of a first bone anchor along a first axis having an angle with the fixed plane that is about 100 degrees (+/−20 degrees); a second hole positioned in the anterior side of the head wherein the second hole passes through the upper and lower surfaces and is configured to fix a shaft of a second bone anchor along a second axis having an angle with the fixed plane that is about 100 degrees (+/−20 degrees); and a third hole positioned in the posterior side of the head wherein the third hole passes through the upper and lower surfaces and is configured to fix a shaft of a third bone anchor along a third axis having an angle with the fixed plane that is about 110 degrees (+/−20 degrees), wherein the first axis, the second axis and the third axis do not intersect in the bone when the plate is in use.

In yet another embodiment of the present invention, an elongated bone plate for treating fractures of the proximal femur comprises a head wherein the head is curved to accommodate the lateral curve of the greater trochanter when the plate is in use; a shaft connected to the head wherein at least a portion of the shaft which overlays the lateral aspect of the subtrochanteric region is thickened; an upper surface; a lower surface intended to be adjacent to the patient's bone when the plate is in use and wherein the shaft has a substantially fixed plane. The plate includes a first hole positioned in the head wherein the first hole passes through the upper and lower surfaces and is configured to fix a shaft of a first bone anchor along a first axis having an angle with the fixed plane that is about 100 degrees (+/−20 degrees) and is directed 10 degrees anterior (+/−20 degrees). A second hole positioned in the anterior side of the head wherein the second hole passes through the upper and lower surfaces and is configured to fix a shaft of a second bone anchor along a second axis having an angle with the fixed plane that is about 100 degrees (+/−20 degrees) and is directed 5 degrees anterior (+/−20 degrees). A third hole positioned in the posterior side of the head wherein the third hole passes through the upper and lower surfaces and is configured to fix a shaft of a third bone anchor along a third axis having an angle with the fixed plane that is about 110 degrees (+/−20 degrees) and is directed 5 degrees anterior (+/−20 degrees).

In yet another embodiment of the present invention a method of treating a fracture of the proximal femur comprises applying an elongated bone plate assembly to the lateral aspect of the proximal femur wherein the plate comprises a head; a shaft; an upper surface; a lower surface having a fixed plane intended to be adjacent to the patient's bone when the plate is in use; a first hole positioned in the head wherein the first hole passes through the upper and lower surfaces and is configured to fix a shaft of a first bone anchor along a first axis; a second hole positioned on the anterior portion of the upper surface of the head wherein the second hole passes through the upper and lower surfaces and is configured to fix a shaft of a second bone anchor along a second axis; and a third hole positioned in the posterior side of the head wherein the third hole passes through the upper and lower surfaces and is configured to fix a shaft of a third bone anchor along a third axis; wherein the first axis, the second axis and the third axis do not intersect in the bone when the plate is in use. The plate is secured to the bone with a bone anchor inserted through any one of a first bone anchor hole, a second bone anchor hole, a third bone anchor hole or any combination thereof.

DETAILED DESCRIPTION OF THE INVENTION

One embodiment of the present invention is a bone plating system utilizing bone anchors such as cannulated locking screw technology that is indicated for management of certain fractures and nonunions of the proximal femur. However, the system is not limited to cannulated locking screws as other bone anchors such as non-cannulated non-locking screws, variable angle locking screws, fixed angle nails, pins, blades and any combination thereof may be substituted. The plating system is well suited to address certain femoral neck fractures being managed without arthroplasty, particularly vertically oriented fractures, those in which earlier weight bearing is desirable, and those in which a fixed angle device would be beneficial, such as in patients with osteopenia. Bone anchors in the head of the plate are designed to finish in a position for improved management of femoral neck fractures.

Figure 1:
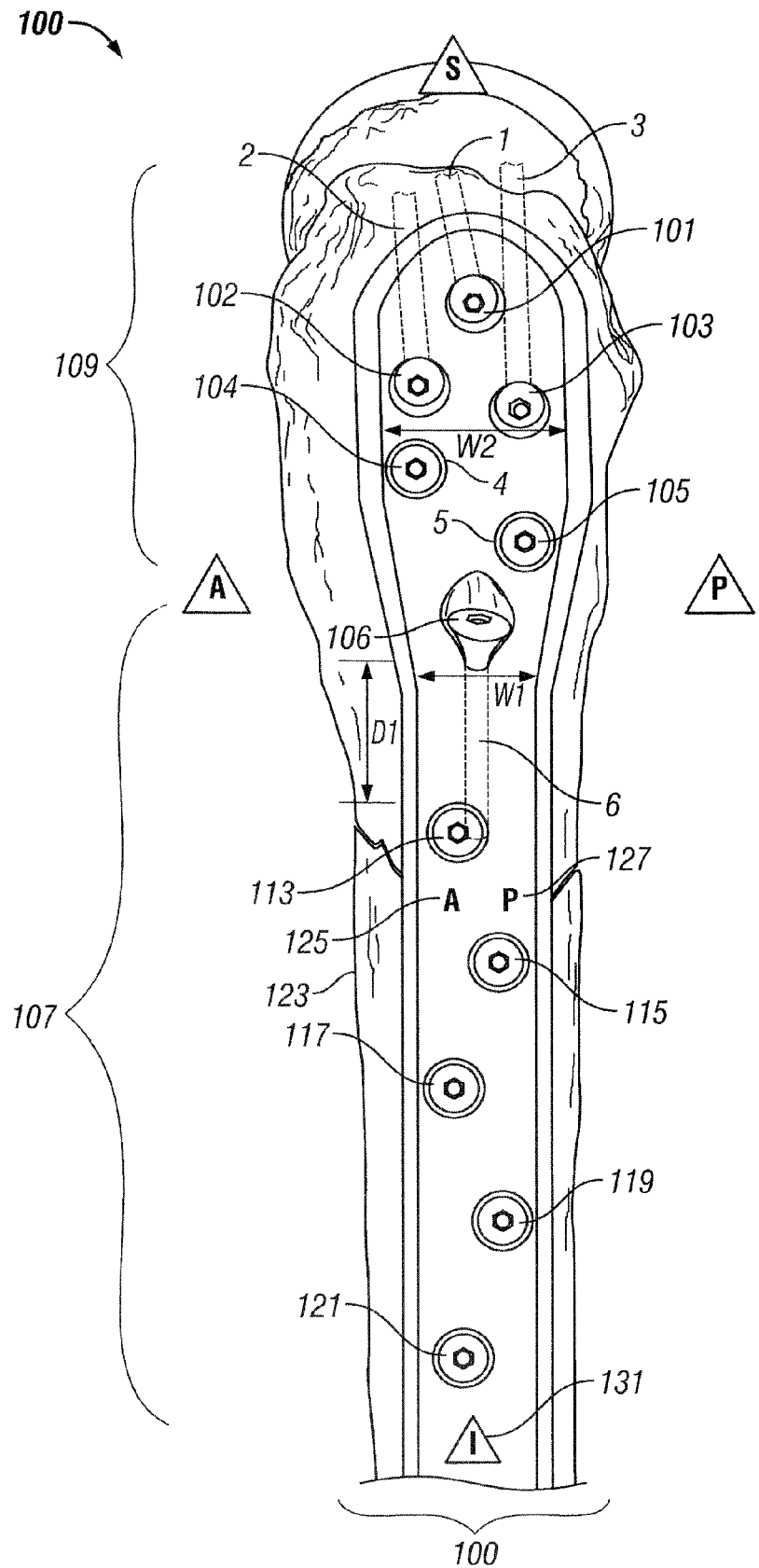
FIG. 1 illustrates a left bone plate according to one embodiment of the present invention for treating nonunions or fractures of a left femur.

Referring now to FIG. 1, a bone plate 100 designed for placement on the lateral aspect of the proximal portion of a human left femur overlying the greater trochanter is illustrated according to one embodiment of the present invention. Lettered triangles refer to the anatomical orientations: A=anterior, S=superior, I=inferior and P=posterior of a left femur in the body. For the purposes of description of embodiment of the present invention, the same nomenclature is used in reference to the bone plate. The shaft 107 of the plate 100 tapers to width w1 in comparison to the head of the plate 109 which broadens to width w2 wherein w2 is wider than w1. The wider head 109 allows for multiple bone anchor holes 101, 102, 103, 104, and 105 to be staggered anterior to posterior in the head 109 of the bone plate to obtain improved finishing positions of the bone anchors 1, 2, 3, in the greater trochanter, neck and femoral head. A widened plate head (from about 2 to about 4 centimeters from anterior to posterior) facilitates capture of greater trochanter extension of intertrochanteric and subtrochanteric fractures, even when there is associated coronal splitting of the greater trochanter. Furthermore, the widened plate head facilitates the improved finishing position of the femoral bone anchors in the femoral head. In another embodiment the head and shaft are the same width.

In one embodiment bone anchor holes 102 and 104 are located on the anterior portion 125 of the left bone plate. The anterior portion 125 of the bone plate is adjacent to the anterior aspect of the left femur 123 when the plate is applied to the lateral aspect of the left femur. Bone anchor holes 103 and 105 are located on the posterior portion of the plate 127. The posterior portion of the plate 127 is adjacent to the posterior aspect of the femur 129 when the bone plate is in use. In a preferred embodiment, bone anchor hole 102 is superior to bone anchor hole 103. In a more preferred embodiment, bone anchor hole 101 is superior to bone anchor hole 102. In a further embodiment, bone anchor hole 101 is on a first longitudinal axis, bone anchor hole 102 is on a second longitudinal axis, and bone anchor hole 103 is on a third longitudinal axis wherein the second and third longitudinal axis may be the same or different from each other and the same or different from the first longitudinal axis. A left bone plate is the mirror image of the right bone plate.

Bone anchors are positioned in one or more bone anchor holes 101, 102, 103, 104, 105, 106, 113, 115, 117, 119, and 121 to secure the bone plate to the bone. The bone anchors 1, 2, 3, 4 and 5 are positioned in the head 109 of the bone plate 100 while bone anchor 6 when present is positioned in the shaft 107 of the bone plate 100 through bone anchor hole 106. The area d1 between the upper surface and the lower surface may be thickened with respect to the thickness of the remainder of the plate. In a preferred embodiment the head of the bone anchors finish flush with the bone plate. When the head portion of the bone plate is properly positioned on the greater trochanter, bone anchor hole 101 directs a bone anchor 1 to enter the greater trochanter and finish in the femoral head at about center position. Bone anchor hole 103 directs a bone anchor 3 to enter the greater trochanter and finish in the femoral head at about the center posterior position along the posterior neck (to address failure in retroversion). Bone anchor hole 102 directs a bone anchor that enters the greater trochanter to finish in the femoral head at center inferior along the inferior neck (to address failure in varus). In a preferred embodiment bone anchor 3 will finish behind bone anchor 1.

In a preferred embodiment the bone anchor holes 101, 102, 103, 104, and 105 in the bone plate head 109 are about 3-30 millimeters apart from each other as measured from the center of each bone anchor hole to achieve a sufficient bone anchor spread finishing distance in the femoral head. For example the distance is about 6-30 millimeters. In a preferred embodiment a head is between about 2-4 centimeters wide and the spread between holes 101, 102, and 103 is about 10-20 millimeters.

In a preferred embodiment, the engagement of the bone anchors with the plate may fix the bone anchors in a position that does not permit the bone anchors to touch or form a truss in the bone In another embodiment, a downward angling bone anchor 6 is positioned at bone anchor hole 106 in the proximal shaft of the plate to allow capturing of the medial femoral spike in reverse oblique fractures, and a long zone of thickening d1 with no holes machined in this zone allows for greater fatigue resistance. Alternatively a bone anchor hole is present in position d1.

In a preferred embodiment bone anchor holes 102 and 103 do not lie in the same longitudinal axis with bone anchor hole 101 as is required with other bone plates designed to treat fractures of the proximal femur. In a more preferred embodiment, a least one bone anchor hole does not lie along the same longitudinal axis with bone anchor hole 101. In a preferred embodiment bone anchor hole, 101 is positioned about center on the plate.

In a preferred embodiment the bone plate is metal for example stainless steel or titanium. In another preferred embodiment, at least a portion of the head is curved upward from plane P of the shaft. For example the head of the plate is pre-contoured or curved to the shape of the lateral aspect of the greater trochanter. At least a portion of the body of the plate may be thickened proximally which extends a variable length down the lateral shaft of the femur. The thickness of the plate ranges from about 1 to about 5 millimeters at the proximal tip to about 5 to about 15 millimeters at the portion of the shaft that overlays the subtrochanteric region of the femur when the plate is in use. The shaft tapers to about 3 to about 7 millimeters at the distal end of the shaft. In another embodiment the plate is of uniform thickness.

The head of the plate has a width which ranges from 2 to 4 centimeters and tapering to 1 to 3 centimeters at the shaft or body of the plate. The length of the plate ranges from about 10 to 16 centimeters (for example a plate with two body holes) to over about 30 centimeters. Plates with more than six bone anchor holes may be bowed to match the natural curvature of the lateral femur.

Figure 2:
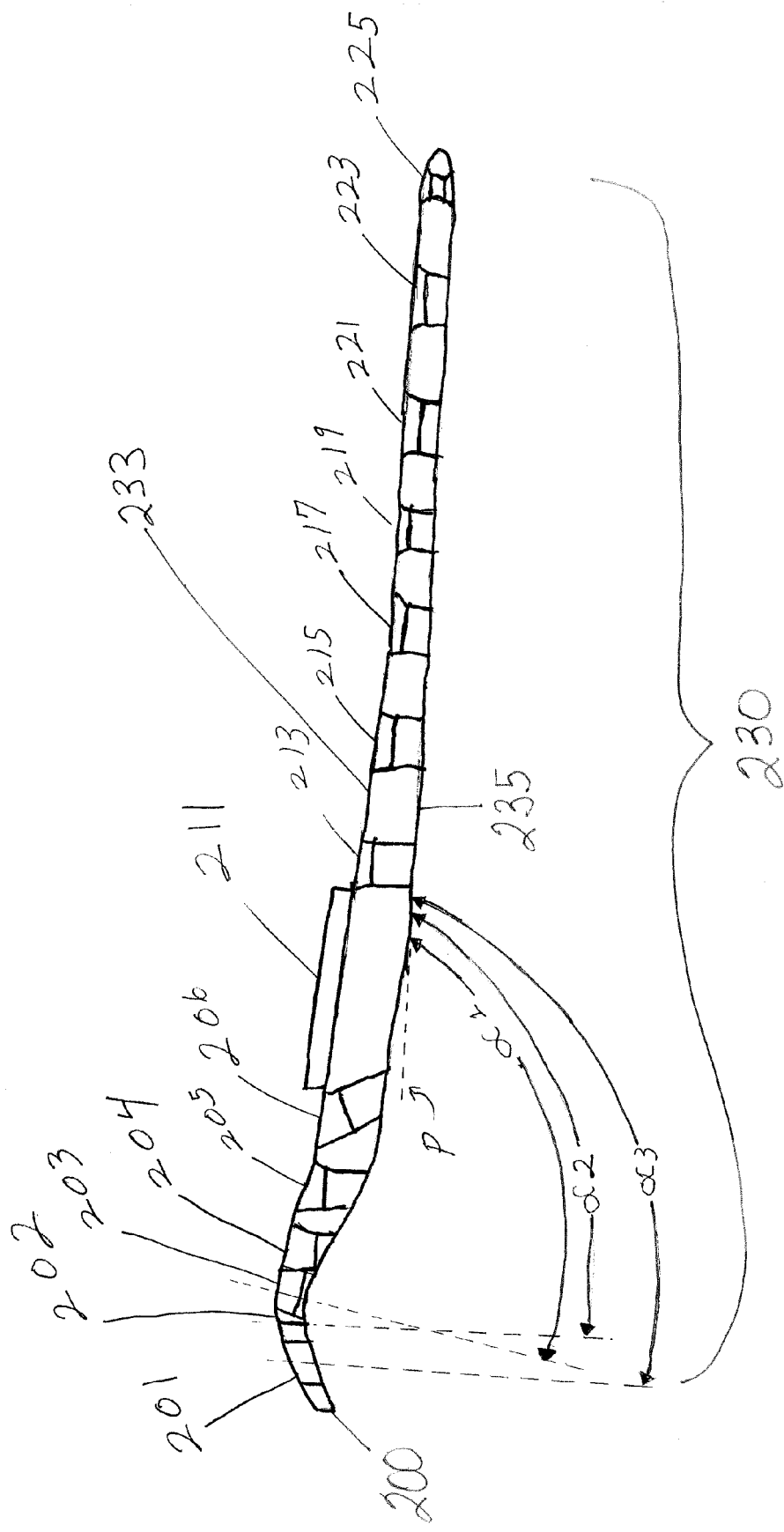
FIG. 2 illustrates a side view of one embodiment of the present invention.

Referring now to FIG. 2, bone plate 230 has an upper surface 233 and a lower surface 235. A bottom plane "P" is identified on the bottom surface 235 of plate 230. A proximal end of the plate 200, including the head, is contoured to the shape of the lateral aspect of the greater trochanter of the femur. Plate 230 is further described in relation to the anterior, superior, inferior and posterior anatomical orientation of the femur in the body upon which the plate is applied. Bone anchor hole 201 aims a bone anchor 10 degrees anterior and 10 degrees superior from a 90 degree angle with plane P to form central axis F. An angle $\alpha 3$ of about 100 degrees is formed between central axis F and plane P. Bone anchor hole 202 aims 5 degrees anterior and 10 degrees superior from a 90 degree angle with plane P to form central axis D. An angle $\alpha 2$ of about 100 degrees is formed with respect to central axis D and plane P. Bone anchor hole 203 aims 5 degrees anterior and 20 degrees superior from a 90 degree angle with plane P to form central axis E. An angle $\alpha 1$ of about 110 degrees is formed between central axis E and plane P. Bone anchor hole 204 and 205 aim 0 degrees anterior and 0 degrees superior from a 90 degree angle with plane P with respect to the body of the plate. All measurements are with respect to locking screws. (In Substantial thickening of the shaft of the plate (from 6 to 15 millimeters) with avoidance of screw holes (stress risers) in the region distal to bone anchor hole 206 is illustrated at 211. The thickening is to assist with fatigue resistance at the subtrochanteric region of the femur. Because the subtrochanteric region of the femur is well lateral to the mechanical axis of the lower extremity, it experiences very high tensile and compressive forces.

In one embodiment of the present invention bone anchor holes 201-206 accept locked and unlocked screws between about 4 and about 8 millimeters in diameter and cannulated screw with a cannula of about 1 to about 4 millimeters in diameter. Bone anchor hole number 206 and bone anchor holes in the shaft 213, 215, 217, 219, 221, 223, and 225 accept locked and unlocked solid screws between about 3 and about 6 millimeters but are not limited thereto.

Bone anchor hole 206 is positioned through the proximal body of the plate via a locking or non-locking hole that aims about 35 to about 55 degrees distally to capture the medial femoral cortex in reverse oblique fracture patterns when the plate is in use. In a preferred embodiment, the hole aims about 45 degrees distally from bone anchor hole 206. Distal to bone anchor hole 206, zone 211 consists of a zone about 2 to about 5 centimeters of thickening with no holes machined in it to improve fatigue resistance. In another embodiment, the body is not thickened and may contain one or more bone anchor holes.

Moving distal to the zone of fatigue resistance, bone anchor holes for the femoral shaft begin with a spacing of about 1 to about 3 centimeters with a coronal plane staggering of about 0 to about 6 millimeters. In a preferred embodiment, the distal tip of the plate is tapered to a sharp edge to facilitate percutaneous placement. Additionally, the proximal tip of the head of the bone plate may be tapered as to width and thickness. A bone hook may be added to the widened head to assist in holding comminuted fragments of a greater trochanter. One or more of the bone anchor holes in the shaft may be on the same or a different longitudinal axis.

According to one embodiment there is an external insertion guide which can attach to one or more of the proximal screw holes to allow percutaneous placement of the plate. This is also facilitated by a sharp distal tapering of the plate. The insertion guide may be made of a material that is radiolucent for example.

Bone anchor hole 206 directs a downward directed screw for direct interfragmentary fixation of reverse oblique fracture patterns and nonunions. Bone anchor hole 206 directs a bone anchor into the bone on an axis that forms an approximate 35 to 55 degree distally downward directed angle with the plane for interfragmentary fixation of this challenging fracture pattern. The screw hole is above the zone of the subtrochanteric zone of the plate. Excellent compression across a reverse oblique nonunion site may be achieved with the downward directed screw.

Figure 3:
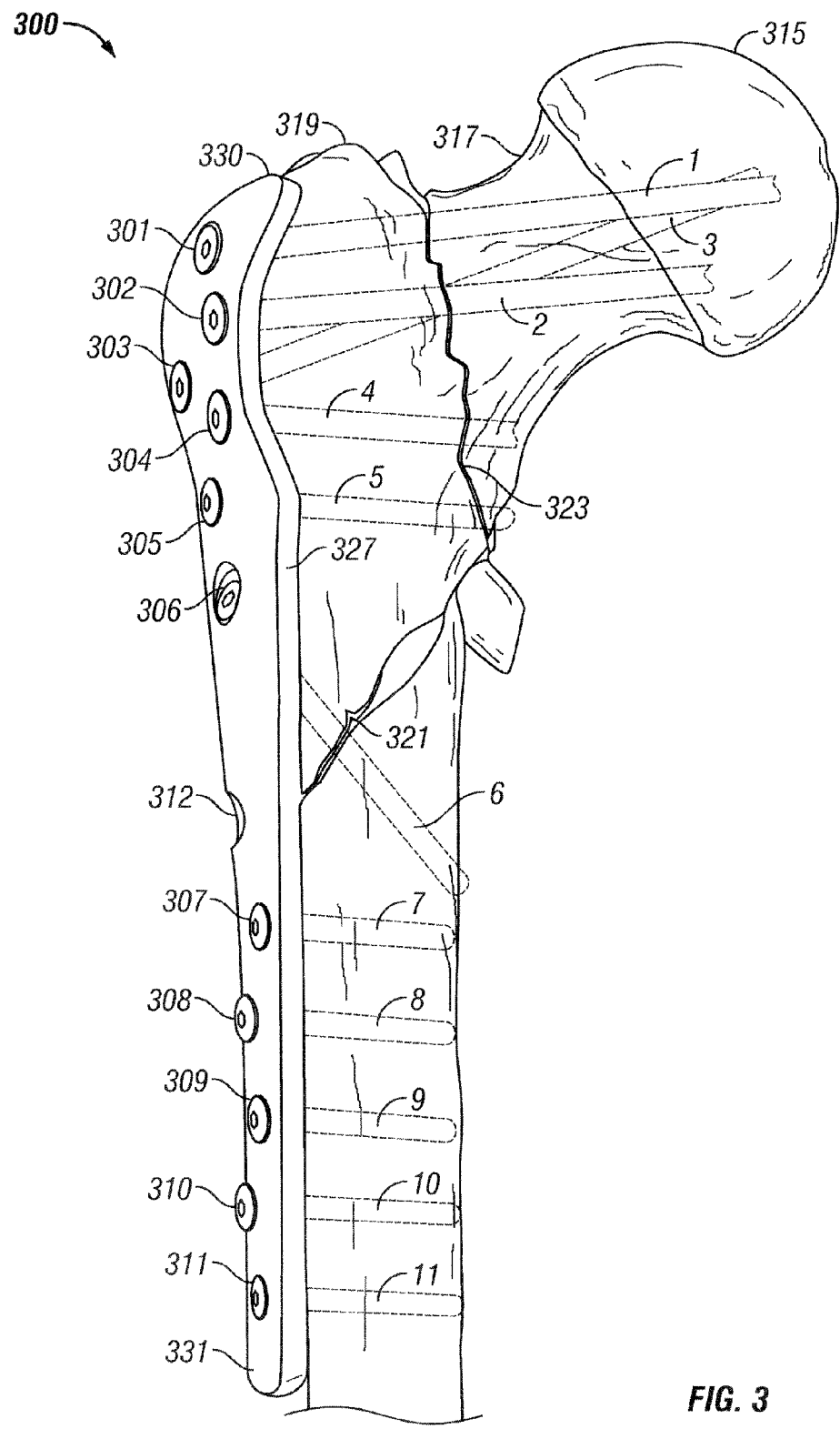
FIG. 3 illustrates an anterior posterior view of a right bone plate according to one embodiment of the present invention for treating fractures of the right femur.

Referring now to FIG. 3, a right bone anchor plate in use on a right femur is illustrated according to one embodiment of the present invention. Plate 300 displays a plurality of bone anchor holes 301, 302, 303, 304, 305, 306, 307, 308, 309, 310, and 311. The plurality of holes are engineered to create fixed angles at which bone anchors are directed when passed through the bone anchor hole. Bone anchor hole 301 is engineered to make bone anchor 1 finish in the femoral head 315 at center after passing through the neck 317 and greater trochanter 319. Bone anchor hole 302 is positioned on the anterior side of the plate 327 and is engineered to make bone anchor 2 finish in the femoral head at center inferior along the inferior neck when the plate is centered on the lateral femur with the curved head not extending past the top of the greater trochanter. Bone anchor hole 303 is positioned on the posterior side of the plate and is engineered to make bone anchor 3 finish in the femoral head at center posterior along the posterior neck. The positioning of bone anchors 1, 2 and 3 in the proximal femur may address fractures 323. Bone anchor holes 304 and 305 are engineered to direct bone anchors 4 and 5 into the lower portion of the greater trochanter and medial femoral neck. Bone anchor 6 is directed along an axis by bone anchor hole 306 at about 45 degree angle which is suited to address fracture 321. One or more of bone anchors 7, 8, 9, 10, 11 further secure the plate to the bone through corresponding bone anchor holes 307, 308, 309, 310 and 311.

Figure 4:
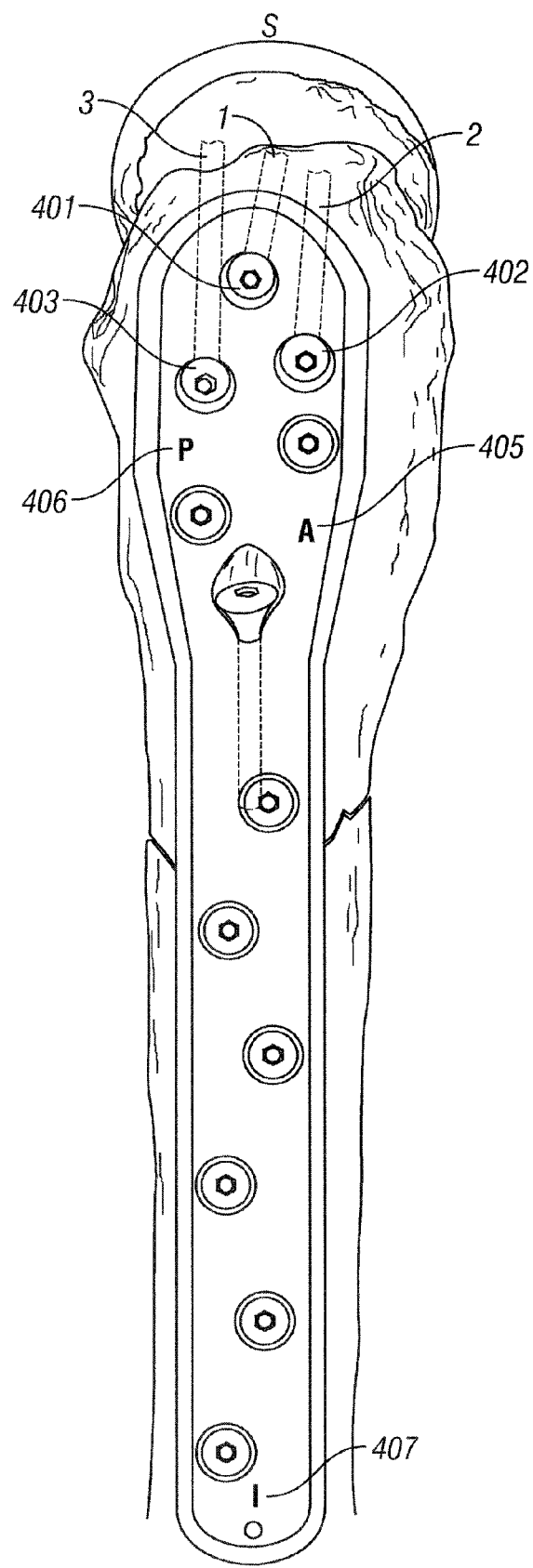
FIG. 4 illustrates a right bone plate on a right femur that is the mirror image of the left bone plate.

Referring now to FIG. 4, a right femur plate in use on a right femur is illustrated according to one embodiment of the present invention. The right femur plate is the mirror image of the left femur plate of FIG. 1. Superior orientation 409 is denoted as "S" while anterior 405, posterior 406, and inferior 407 orientation are denoted as "A", "P", and "I" respectively. Bone anchor hole 401 directs bone anchor 1 at a first axis. Bone anchor hole 402 directs bone anchor at a second axis. Bone anchor hole 403 directs bone anchor 3 at a third axis. The first axis, the second axis and the third axis do not form a single plane.

The present invention has been described in terms of preferred embodiments, however, it will be appreciated that various modifications and improvements may be made to the described embodiments without departing from the scope of the invention. The entire disclosures of all references, applications, patents, and publications cited above and/or in the attachments, and of the corresponding application(s), are hereby incorporated by reference.

The invention claimed is:

1. An elongated bone plate for treating fractures of a proximal femur comprising:
    a head that is curved to conform to a contour of a greater trochanter of the proximal femur;
    a shaft that is narrower than the head and configured to conform to the lateral shaft of the proximal femur;
    an upper surface;
    a lower surface having a fixed plane intended to be adjacent to the lateral shaft of a the proximal femur when the plate is in use;
    a first hole positioned in the head wherein the first hole passes through the upper and lower surfaces and is configured to fix a shaft of a first bone anchor along a first axis;
    a second hole positioned on the anterior portion of the upper surface of the head wherein the second hole passes through the upper and lower surfaces and is configured to fix a shaft of a second bone anchor along a second axis; and
    a third hole positioned in the posterior side of the head wherein the third hole passes through the upper and lower surfaces and is configured to fix a shaft of a third bone anchor along a third axis,
    wherein the first axis, the second axis and the third axis pass entirely through the neck of the proximal femur without breaching a side surface thereof and do not intersect in the head of the proximal femur when the plate is in use and wherein the first hole, the second hole and the third hole are arranged in a triangular pattern on the upper surface of the head of the bone plate to guide a plurality of bone anchors to enter the greater trochanter through the first hole, the second hole and the third hole to cause the plurality of bone anchors to finish in the femoral head.

2. The bone plate of claim 1 wherein the head is between about 2 to about 4 centimeters from anterior to posterior.

3. The bone plate of claim 1 wherein the head has a thickness of between about 1 to about 5 millimeters.

4. The bone plate of claim 1 wherein the shaft has a thickness of between about 3 to about 15 millimeters.

5. The bone plate of claim 1 wherein the first axis has an angle with the fixed plane that is about 100 degrees (+/−20 degrees) and is directed 10 degrees anterior (+/−20 degrees).

6. The bone plate of claim 1 wherein the second axis has an angle with the fixed plane that is about 100 degrees (+/−20 degrees) and is directed 5 degrees anterior (+/−20 degrees).

7. The bone plate of claim 1 wherein the third axis has an angle with the fixed plane that is about 110 degrees (+/−20 degrees) and is directed 5 degrees anterior (+/−20 degrees).

8. The bone plate of claim 1 further comprising a fourth hole positioned in the posterior side of the head wherein the fourth hole passes through the upper and lower surfaces and is configured to fix a shaft of a fourth bone anchor along a fourth axis.

9. The bone plate of claim 1 further comprising a fourth hole positioned in the proximal shaft wherein the fourth hole passes through the upper and lower surfaces and is configured to fix a shaft of a fourth bone anchor along a fourth axis.

10. The bone plate of claim 9 wherein the fourth axis has an angle with the fixed plane that is about 45 degrees (+/−20 degrees).

11. The bone plate of claim 1 wherein a portion of the shaft has a thickness of between about 6 to about 15 millimeters and when in use overlays the subtrochanteric region of the proximal femur.

12. The bone plate of claim 1 wherein the first axis, the second axis and the third axis are fixed by the plate.

13. The bone plate of claim 1 wherein the first hole, the second hole and the third hole are engineered and designed to have an orientation such that the first axis, the second axis and the third axis are not surgeon selectable but instead are determined during design of the bone plate.

14. An elongated bone plate for treating fractures of the proximal femur comprising:
   a head wherein at least a portion of the head is curved to conform to the contour of the greater trochanter;
   a shaft wherein at least a portion of the shaft is thickened and wherein the shaft is narrower than the head;
   an upper surface;
   a lower surface wherein the lower surface has a substantially fixed plane intended to be adjacent to the greater trochanter and lateral shaft of the proximal femur when the plate is in use;
   a first hole positioned in the head wherein the first hole passes through the upper and lower surfaces and is configured to fix a shaft of a first bone anchor along a first axis to finish in the femoral head with the first axis having an angle with the fixed plane that is about 100 degrees (+/−20 degrees);
   a second hole positioned in the anterior side of the head wherein the second hole passes through the upper and lower surfaces and is configured to fix a shaft of a second bone anchor along a second axis to finish in the femoral head with the second axis having an angle with the fixed plane that is about 100 degrees (+/−20 degrees); and
   a third hole positioned in the posterior side of the head wherein the third hole passes through the upper and lower surfaces and is configured to fix a shaft of a third bone anchor along a third axis to finish in the femoral head with the third axis having an angle with the fixed plane that is about 110 degrees (+/−20 degrees),
   wherein the first axis, the second axis and the third axis do not intersect in the femoral head when the plate is in use and wherein the first hole the second hole and the third hole form a triangular pattern on the upper surface of the head of the bone plate the first second and third axes pass entirely through the neck of the proximal femur without breaching a side surface thereof.

15. The bone plate of claim 14 further comprising a fourth hole positioned in the proximal shaft wherein the fourth hole passes through the upper and lower surfaces and is configured to fix a shaft of a fourth bone anchor along a fourth axis having an angle with the fixed plane that is about 45 degrees (+/−20 degrees).

16. An elongated bone plate for treating fractures of the proximal femur comprising:
   a head that is curved to contour to the lateral curve of the greater trochanter when the plate is in use;
   a shaft connected to the head wherein at least a portion of the shaft which overlays the lateral aspect of the subtrochanteric region is thickened;
   an upper surface;
   a lower surface intended to be adjacent to the patient's bone when the plate is in use and wherein the shaft has a substantially fixed plane;
   a first hole positioned in the head wherein the first hole passes through the upper and lower surfaces and is configured to fix a shaft of a first bone anchor along a first axis that finishes within the femoral head with the first axis having an angle with the fixed plane that is about 100 degrees (+/−20 degrees) and is directed 10 degrees anterior (+/−20 degrees);
   a second hole positioned in the anterior side of the head wherein the second hole passes through the upper and lower surfaces and is configured to fix a shaft of a second bone anchor along a second axis that finishes within the femoral head with the second axis having an angle with the fixed plane that is about 100 degrees (+/−20 degrees) and is directed 5 degrees anterior (+/−20 degrees);
   a third hole positioned in the posterior side of the head wherein the third hole passes through the upper and lower surfaces and is configured to fix a shaft of a third bone anchor along a third axis that finishes within the femoral head with the third axis having an angle with the fixed plane that is about 110 degrees (+/−20 degrees) and is directed 5 degrees anterior (+/−20 degrees);
   wherein each of the axes of the first, second, and third holes pass entirely through the neck of the proximal femur without breaching a side surface thereof; and
   a fourth bone anchor hole positioned through the proximal body of the plate below the head via a locking or non-locking hole that aims about 35 to about 55 degrees distally to capture the medial femoral cortex in reverse oblique fracture patterns when the plate is in use.

17. A method of treating a fracture of the proximal femur comprising:
   applying an elongated bone plate assembly to the lateral aspect of the proximal femur wherein the plate comprises:
   a head that is curved to conform to the contour of the greater trochanter;
   a shaft that is narrower than the head and configured to conform to the lateral shaft of the proximal femur;
   an upper surface;
   a lower surface having a fixed plane intended to be adjacent to the lateral shaft of the proximal femur when the plate is in use;
   a first hole positioned in the head wherein the first hole passes through the upper and lower surfaces and is configured to fix a shaft of a first bone anchor along a first axis;
   a second hole positioned on the anterior portion of the upper surface of the head wherein the second hole passes through the upper and lower surfaces and is configured to fix a shaft of a second bone anchor along a second axis; and
   a third hole positioned in the posterior side of the head wherein the third hole passes through the upper and lower surfaces and is configured to fix a shaft of a third bone anchor along a third axis;
   the first, second, and third axes pass entirely through the neck of the proximal femur without breaching a side surface thereof;
   wherein the first axis, the second axis and the third axis do not intersect in the femoral head when the plate is in use and wherein the first hole, the second hole and the third hole form a triangular pattern in the upper surface of the head of the bone plate; and
   securing the plate to the proximal femur through the greater trochanter with a plurality of bone anchors inserted through the first hole, the second hole, the third hole or any combination thereof to cause the plurality of bone anchors to finish in the femoral head.

18. The apparatus of claim 1 further comprising a fourth bone anchor hole positioned through the proximal body of the plate via a locking or non-locking hole that aims about 35 to about 55 degrees distally to capture the medial femoral cortex in reverse oblique fracture patterns when the plate is in use.

19. The apparatus of claim 18 wherein the fourth bone anchor hole aims about 45 degrees distally from the fourth bone anchor hole.

20. The apparatus of claim 18 wherein distal to the fourth bone anchor hole a zone consists of about 2 to about 5 centimeters of thickening with no holes machined in it to improve fatigue resistance.

* * * * *